United States Patent [19]
Wachter et al.

[11] 4,096,253
[45] Jun. 20, 1978

[54] 1-OXYGENATED STEROIDS

[75] Inventors: Michael P. Wachter, Bloomsbury, N.J.; Joseph A. Settepani, Vienna, Va.

[73] Assignee: Ortho Pharmaceutical Corporation, Raritan, N.J.

[21] Appl. No.: 703,049

[22] Filed: Jul. 6, 1976

[51] Int. Cl.$^2$ .................... C07J 17/00; C07J 1/00
[52] U.S. Cl. .................... 424/238; 260/239.55 R; 260/397.4; 260/397.5
[58] Field of Search ............. 260/397.4, 397.5, 239.55

[56] References Cited

U.S. PATENT DOCUMENTS

| 3,951,958 | 4/1976 | Prezewowsky | 260/239.5 |
| 3,951,959 | 4/1976 | Prezewowsky | 260/239.55 D |

Primary Examiner—Elbert L. Roberts
Attorney, Agent, or Firm—Benjamin F. Lambert

[57] ABSTRACT

1-Oxygenated steroids and a method of preparing same as described. The 1-oxygenated steroids are useful as antifertility agents.

11 Claims, No Drawings

1-OXYGENATED STEROIDS

This invention relates to certain 1-oxygenated steroids which are active antifertility agents. The compounds exhibit anti-implantive activity and are useful in the suppression of reproduction in female animals.

The compounds which are the subject of this invention are represented by the formulae:

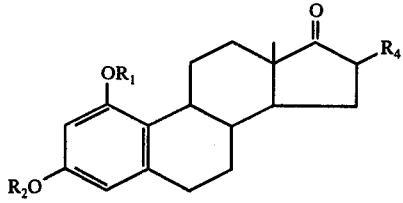

I

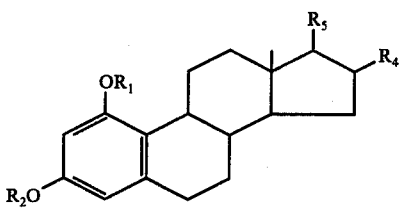

II

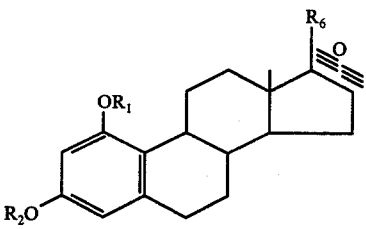

III

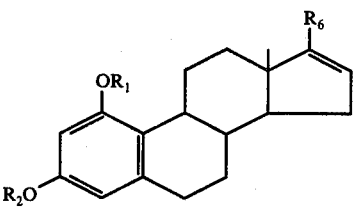

IV

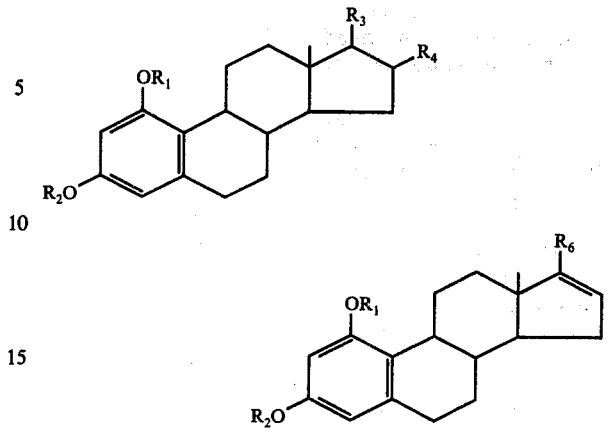

wherein $R_1$ is lower alkanoyl wherein the alkanoyl group has 2-6 carbon atoms, lower alkyl wherein the alkyl group has 1-5 carbon atoms and trialkylaminosulfoxy wherein the alkyl group has 1-3 carbon atoms; $R_2$ is lower alkyl wherein the alkyl group has 1-5 carbon atoms and trialkylaminosulfoxy wherein the alkyl group has 1-3 carbon atoms; $R_4$ is hydrogen, halogen, such as fluoro, chloro, or bromo, lower alkanoyloxy wherein the alkanoyloxy group has 2-5 carbon atoms and hydroxy; $R_5$ is lower alkoxy, wherein the alkoxy group has 1-5 carbon atoms, lower alkanoyloxy wherein the alkanoyloxy group has 1-5 carbon atoms, cyanoethoxy, hydroxy and trifluoroalkanoyloxy wherein the alkanoyloxy group has 2-5 carbon atoms; and $R_6$ is hydroxy or lower alkanoyloxy wherein the alkanoyloxy group has 2-5 carbon atoms; provided that in formula I when $R_2$ is lower alkyl and $R_4$ is hydrogen, $R_1$ is not lower alkanoyl or lower alkyl.

Preferred among the compounds of the present invention are those compounds having the formulae:

wherein $R_1$ is lower alkanoyl wherein the alkanoyl group has 2-6 carbon atoms, lower alkyl wherein the alkyl group has 1-5 carbon atoms and trialkylaminosulfoxy wherein the alkyl group has 1-3 carbon atoms; $R_2$ is lower alkyl wherein the alkyl group has 1-5 carbon atoms and trialkylaminosulfoxy wherein the alkyl group has 1-3 carbon atoms; $R_3$ is oxo, lower alkanoyloxy wherein the alkanoyloxy group has 2-5 carbon atoms, lower alkoxy wherein the alkoxy group has 1-5 carbon atoms, hydroxy, cyanoethoxy and trifluoroalkanoyloxy wherein the alkanoyloxy group has 2-5 carbon atoms; and $R_4$ is halogen, lower alkanoyloxy wherein the alkanoyloxy group has 2-5 carbon atoms and hydroxy; provided that when $R_3$ is other than oxo, $R_4$ may also be hydrogen, except that where $R_1$ and $R_2$ are trialkylaminosulfoxy, $R_3$ may be oxo and $R_4$ may be hydrogen; and $R_6$ is hydroxy or lower alkanoyloxy.

The 1-oxygenated steroids which are the subject of this invention are prepared by reacting an appropriately substituted estratriene derivative with a suitable reagent to form the desired compound. Those compounds having a trialkylaminosulfoxy group in the 1 or 3 position are prepared by reacting an appropriately substituted 1- or 3-hydroxyestratriene-17-one with an appropriate trialkylamine complex such as, for example, sulfur trioxide triethylamine complex, in a suitable base such as anhydrous pyridine. Those compounds wherein $R_1$ or $R_2$ is lower alkyl can be prepared by reacting an appropriately substituted 1-oxygenated-3-hydroxyestra-1,3,5(10)-trien-17-one, for example, with a suitable alkylating agent such as, for example, diazomethane, dimethyl sulfate, methyl iodide, butyl bromide and the like.

Those compounds wherein $R_3$ or $R_5$ is hydroxy can be prepared by reduction of a suitably substituted 1-oxygenated estra-1,3,5(10)-trien-17-one. Reducing agents which may be employed include platinum oxide, palladium and sodium borohydride. Those compounds containing a double bond at the 16-17 position can be prepared, for example, by reacting an appropriately substituted 17-keto derivative with an alkyl ester such as isopropenyl acetate at elevated temperatures. Those compounds wherein $R_3$ is oxo and $R_4$ is halogen can be prepared by reacting an appropriately substituted 1-oxygenated steroid having a double bond in the 16-17 position with a halogen. Those compounds wherein $R_5$ is trifluoroalkanoyloxy can be prepared by reacting an appropriately substituted 1-oxygenated-estra-1,3,5(10)-trien-17β-ol with an appropriate anhydride such as, for example, trifluoroacetic anhydride. Those compounds wherein $R_5$ is cyanoethoxy are prepared by reacting an appropriately substituted 17-hydroxy-1,3,5(10)-estratriene with an appropriate nitrile such as, for example, acrylonitrile in the presence of a base. Those compounds having an epoxide ring at the 16-17 position can be prepared by reacting an appropriately substituted 1-oxygenated compound which is unsaturated at the 16-17 position with a peracid such as, for example, perbenzoic acid.

The 1-oxygenated steroids of the present invention possess pharmacological activity as antilittering agents. They are useful, therefore, as agents for the suppression of reproduction. The compounds can be administered orally to female animals and are effective post-implantive agents. The compounds are active at dose levels ranging from about 0.25 mg to about 10 mg. The anti-implantive activity of the compounds is determined as follows:

Adult female Wistar rats are smeared daily and cohabited continuously with males of proven fertility. Each morning the females are examined for the presence of sperm in vaginal washings. The day on which sperm are found constitutes day 1 of pregnancy. Pregnant rats receive the test compound dissolved in sesame oil by gavage on day 1 through day 6 of pregnancy for studies of anti-implantive activity or on days 7 through 12 for studies of post-implantive effects. They are sacrificed on day 20 for examination of uterine contents. The number of implantations and their appearance are recorded. Controls receive only the vehicle.

EXAMPLE 1

1-Acetoxy-3-methoxyestra-1,3,5(10)-trien-17β-ol

A solution of 1-acetoxy-3-methoxyestra-1,3,5(10)-trien-17-one (4.9 g, 14.3 mM) in 250 ml of ethanol is shaken with $PtO_2$ (1 g) under $N_2$ at 40 psi for 7 hrs. After filtration and evaporation of the solvent in vacuo, the oily residue is chromatographed on 250 g of neutral silica gel, initially eluting with benzene and finally progressing to 5% ethyl acetate:benzene. Evaporation of the solvent in vacuo, followed by recrystallization from ether:hexane gives 1-acetoxy-3-methoxyestra-1,3,5(10)-trien-17β-ol, yield 2.35 g (48%), m.p. 107°–110° C.

When in the above procedure 3-methoxy-1-propionyloxyestra-1,3,5(10)-trien-17-one and 1-butyryloxy-3-propoxyestra-1,3,5(10)-trien-17-one are employed in place of 1-acetoxy-3-methoxyestra-1,3,5(10)-trien-17-one, 3-methoxy-1-propionyloxyestra-1,3,5(10)-trien-17β-ol and 1-butyryloxy-3-propoxyestra-1,3,5(10)-trien-17β-ol are obtained.

EXAMPLE 2

1-Acetoxy-3,17β-dimethoxy-1,3,5(10)-estratriene

1-Acetoxy-3-methoxyestra-1,3,5(10)-trien-17β-ol (1.0 g) is etherified with $CH_2H_2$, generated from N-nitrosomethylurea and catalyzed with a drop of 48% $HBF_4$ in methylene chloride. The resulting polymethylene polymer is filtered and the methylene chloride filtrate is washed with 10% sodium bicarbonate solution, water and then dried over sodium sulfate. Evaporation in vacuo gives an oil which is crystallized from ethanol to give 1-acetoxy-3,17β-dimethoxy-1,3,5(10)-estratriene as a white solid, yield 0.78 g (75%); m.p. 81°–83° C.

When in the above procedure 1-acetoxy-3-ethoxyestra-1,3,5(10)-trien-17β-ol and 1-propionyloxy-3-butoxyestra-1,3,5(10)-trien-17β-ol are employed in place of 1-acetoxy-3-methoxyestra-1,3,5(10)-trien-17β-ol, 1-acetoxy-3-ethoxy-17-methoxyestra-1,3,5(10)-triene and 1-propionyloxy-3-butoxy-17-methoxyestra-1,3,5(10)-triene are obtained.

EXAMPLE 3

1-Acetoxy-3-sulfooxyestra-1,3,5(10)-trien-17-one triethylammonium salt

A solution of 1-acetoxy-3-hydroxyestra-1,3,5(10)-trien-17-one (5.0 g, 15.1 mM) and purified sulfur trioxide triethylamine complex (3.18 g, 17.6 mM) in 20 ml of anhydrous pyridine are heated at 70° for 4 hrs. The resulting solution is stirred an additional 16 hrs at room temperature, added slowly to 1000 ml of anhydrous ether and then allowed to stand for 1 hr. The filtrate is decanted; the gummy residue is washed further with anhydrous ether and chromatographed on 200 g of neutral silica gel. Elution with acetone gives 1-acetoxy-3-sulfooxyestra-1,3,5(10)-trien-17-one triethylammonium salt as a white solid, yield 3.7 g (49%); m.p. 131°–133°.

When in the above procedure 1,3-dihydroxyestra-1,3,5(10)-trien-17-one and 1-propionyloxy-3-hydroxyestra-1,3,5(10)-trien-17-one are employed in place of 1-acetoxy-3-hydroxyestra-1,3,5(10)-trien-17-one, 1,3-disulfooxyestra-1,3,5(10)-trien-17-one bis(triethylammonium) salt and 1-propionyloxy-3-sulfooxyestra-1,3,5(10)-trien-17-one triethylammonium salt are obtained.

EXAMPLE 4

3-Methoxy-1-sulfooxyestra-1,3,5(10)-trien-17-one triethylammonium salt

A solution of 1-hydroxy-3-methoxyestra-1,3,5(10)-trien-17-one (2.3 g, 7.7 mM) and purified sulfur trioxide triethylamine complex (1.63 g, 9 mM) in 15 ml of anhydrous pyridine is heated at 76° for 5 hrs. The resulting dark brown solution is stirred for an additional 60 hrs at room temperature, poured into 500 ml of anhydrous ether and the ether is decanted. The gummy residue is chromatographed on a neutral silica gel column. Elution with 10% methanol: chloroform gives 3-methoxy-1-sulfooxyestra-1,3,5(10)-trien-17-one triethylammonium salt, yield 1.05 g (28%), m.p. 146°–148°.

When in the above procedure 1-hydroxy-3-ethoxyestra-1,3,5(10)-trien-17-one and 1-hydroxy-3-butoxyestra-1,3,5(10)-trien-17-one are employed in place of 1-hydroxy-3-methoxyestra-1,3,5(10)-trien-17-one, 3-ethoxy-1-sulfooxyestra-1,3,5(10)-trien-17-one triethylammonium salt and 3-butoxy-1-sulfooxyestra-1,3,5(10)-trien-17-one triethylammonium salt are obtained.

EXAMPLE 5

1,3-Dimethoxy-17β-hydroxyestra-1,3,5(10)-triene

A solution of 1,3-dimethoxyestra-1,3,5(10)-trien-17-one (2.0 g, 6.4 mM) in 10 ml of anhydrous tetrahydrofuran is added dropwise to a well-stirred suspension of lithium tri-t-butoxyaluminum hydride (4.86 g, 19 mM) in 40 ml of anhydrous tetrahydrofuran at 0°. The suspension is maintained at 0° for 1 hr, warmed to 40° for ½ hr, cooled to room temperature and poured into 200 ml of cold $H_2O$. The basic aqueous solution is extracted with 3 × 50 ml of ether and 3 × 50 ml of methylene chloride. The combined organic extracts are washed with $H_2O$, dried over $Na_2SO_4$ and evaporated in vacuo to give an oily residue which is chromatographed on 100 g of neutral silica gel. Elution with chloroform gives 1,3-dimethoxy-17β-hydroxyestra-1,3,5(10)-triene, yield 1.9 g (95%); m.p. 53°–55° (hexane).

When in the above procedure 1,3-diethoxyestra-1,3,5-(10)-trien-17-one and 1-methoxy-3-ethoxyestra-1,3,5(10)-trien-17-one are employed in place of 1,3-dimethoxyestra-1,3,5(10)-trien-17-one, 1,3-diethoxy-17β-hydroxyestra-1,3,5(10)-triene and 3-ethoxy-17β-hydroxy-1-methoxyestra-1,3,5(10)-triene are obtained.

EXAMPLE 6

17β-(2-Cyanoethoxy)-1,3-dimethoxyestra-1,3,5-(10)-triene

A solution of 1,3-dimethoxy-17β-hydroxyestra-1,3,5(10)-triene (1.5 g, 4.7 mM), potassium t-butoxide (0.053 g, 0.47 mM) and acrylonitrile (0.5 g, 9.4 mM) in 25 ml of anhydrous benzene is refluxed with vigorous stirring for 5 hrs. An additional 0.5 g of acrylonitrile and 0.025 g of potassium t-butoxide are added; the solution is refluxed for 2 hrs and allowed to stir at room temperature for 18 hrs. The resulting suspension is filtered and the filtrate evaporated in vacuo to give an oily residue which is chromatographed on 100 g of neutral silica gel. Elution with chloroform gives an oil which after trituration with hexane gives 17β-(2-cyanoethoxy-1,3-dimethoxyestra-1,3,5(10)-triene, yield 1.06 g (60.6%); m.p. 142°–144° (toluene-hexane).

When in the above procedure 1,3-diethoxy-17β-hydroxyestra-1,3,5(10)-triene and 3-ethoxy-17β-hydroxy-1-methoxyestra-1,3,5(10)-triene are employed in place of 1,3-dimethoxy-17β-hydroxyestra-1,3,5(10)-triene, 17β-(2-cyanoethoxy)-1,3-diethoxyestra-1,3,5(10)-triene and 17β-(2-cyanoethoxy)-3-ethoxy-1-methoxyestra-1,3,5(10)-triene are obtained.

EXAMPLE 7

1,17β-Diacetoxy-3-methoxyestra-1,3,5(10)-triene

A solution of 1-acetoxy-3-methoxyestra-1,3,5(10)-triene-17β-ol (0.95 g, 2.8 mM) in 20 ml of acetic anhydride and 5 ml of pyridine is heated on a steam bath for 1 hr. The resulting yellow solution is cooled and poured into 300 ml of cold H₂O. The suspension is filtered, and the resulting white solid is recrystallized from methanol-H₂O to give 1,17β-diacetoxy-3-methoxyestra-1,3,5(10)-triene as a white solid, yield 0.75 g (70%); m.p. 120°–121°.

When in the above procedure 1-acetoxy-3-propoxyestra-1,3,5(10)-trien-17β-ol and 1-acetoxy-3-ethoxyestra-1,3,5(10)-trien-17β-ol are employed in place of 1-acetoxy-3-methoxyestra-1,3,5(10)-trien-17β-ol, 1,17β-diacetoxy-3-propoxyestra-1,3,5(10)-triene and 1,17β-diacetoxy-3-ethoxyestra-1,3,5(10)-triene are obtained.

EXAMPLE 8

1-Acetoxy-3-methoxy-17β-trifluoroacetoxyestra-1,3,5(10)-triene

1-Acetoxy-3-methoxyestra-1,3,5(10)-trien-17β-ol (1.0 g, 2.9 mM) is added to a solution of 25 ml benzene, 0.36 g glacial acetic acid and 3.78 g of trifluoroacetic anhydride through Gooch tubing over a period of 15 mins. The resulting solution is stirred at room temperature for ½ hr, washed with 10% NaHCO₃, H₂O, dried over Na₂SO₄ and evaporated in vacuo to give a white solid which after recrystallization from hexane gives 1-acetoxy-3-methoxy-17β-trifluoroacetoxyestra-1,3,5(10)-triene, yield 1.05 g (82%); m.p. 137°–138°.

When in the above procedure 1,3-diacetoxyestra-1,3,5(10)-trien-17β-ol and 1-acetoxy-3-butoxyestra-1,3,5(10)-trien-17β-ol are employed in place of 1-acetoxy-3-methoxyestra-1,3,5(10)-trien-17β-ol, 1,3-diacetoxy-17β-trifluoroacetoxyestra-1,3,5(10)-triene and 1-acetoxy-3-butoxy-17β-trifluoroacetoxyestra-1,3,5(10)-triene are obtained.

EXAMPLE 9

1,17-Diacetoxy-3-methoxyestra-1,3,5(10),16-tetraene

A solution of 1-acetoxy-3-methoxyestra-1,3,5(10)-trien-17-one (8.84 g, 26 mM), isopropenyl acetate (132 g, 1320 mM) and p-toluenesulfonic acid monohydrate (1.34 g, 7 mM) is heated at 120° in a distilling flask equipped with a 5 inch Vigreaux column to insure slow distillation. After heating at 120° for 16 hrs, 5 ml of distillate is collected. The temperature is increased to 140° and after 45 mins an additional 60 ml of isopropenyl acetate is collected. The residue is poured into 750 ml of ether and the ether solution is extracted with saturated NaHCO₃ solution and H₂O. The ether extract is dried over MgSO₄ and evaporated in vacuo to give a residue containing the enol acetate and recovered starting material as the major components. The residue is chromatographed on 300 g of neutral silica gel and the column is eluted with 0.5% acetone:petroleum ether to give 1,17-diacetoxy-3-methoxyestra-1,3,5(10),16-tetraene, yield 6.1 g (61%); m.p. 118° (petroleum ether).

When in the above procedure 1,3-diacetoxyestra-1,3,5(10)-trien-17-one and 3-ethoxy-1-propionyloxyestra-1,3,5(10)-trien-17-one are employed in place of 1-acetoxy-3-methoxyestra-1,3,5(10)-trien-17-one, 1,3,17-triacetoxyestra-1,3,5(10),16-tetraene and 17-acetoxy-3-ethoxy-1-propionyloxyestra-1,3,5(10),16-tetraene are obtained.

EXAMPLE 10

1,16β-Diacetoxy-3-methoxyestra-1,3,5(10)-trien-17-one

Lead tetraacetate (0.65 g) is added to a solution of 1,17-diacetoxy-3-methoxyestra-1,3,5(10),16-tetraene (0.5 g, 1.3 mM) in 0.5 ml acetic anhydride and 10 ml glacial acetic acid with stirring. Solution occurs after 1 hr and stirring is continued at room temperature for 16 hrs. The resulting dark brown solution is evaporated in vacuo at 40° to give an oily residue which is dissolved in 150 ml of benzene. The benzene solution is then washed with H₂O, 5% NaHCO₃ and saturated NaCl solution. The organic layer is dried over MgSO₄ and evaporated in vacuo to give a white solid. Trituration with ether gives 1,16β-diacetoxy-3-methoxyestra-1,3,5(10)-trien-17-one as a white solid, yield 0.31 g (62%). Recrystallization from methanol gives 1,16β-diacetoxy-3-methoxyestra-1,3,5(10)-trien-17-one having a m.p. of 191°–192°.

When in the above procedure 3-butoxy-1,17-diacetoxyestra-1,3,5(10),16-tetraene and 1,17-diacetoxy-3-propoxy-1,3,5(10),16-tetraene are employed in place of 1,17-diacetoxy-3-methoxyestra-1,3,5(10),16-tetraene, 3-butoxy-1,16β-diacetoxyestra-1,3,5(10)-trien-17-one and 1,16β-diacetoxy-3-propoxyestra-1,3,5(10)-trien-17-one are obtained.

EXAMPLE 11

1-Acetoxy-16α-chloro-3-methoxyestra-1,3,5(10)-trien-17-one

A solution of $Cl_2$ (0.162 g, 2.3 mM) in 5 ml of carbon tetrachloride is added over a period of 30 min to a stirred suspension of 1,17-diacetoxy-3-methoxyestra-1,3,5(10),16-tetraene (0.77 g, 2 mM), $K_2CO_3$ (5 g) and 25 ml of $CCl_4$ at 0°. Dilute aqueous sodium thiosulfate is then added, the layers are separated and the aqueous layer is extracted with 2 × 50 ml chloroform. The organic layers are combined, dried over $MgSO_4$ and evaporated in vacuo. The residue is triturated with ether to give a white solid. Recrystallization from methanol gives 1-acetoxy-16α-chloro-3-methoxyestra-1,3,5(10)-trien-17-one, yield 0.64 g (76%); m.p. 194.5°–196°.

When in the above procedure 1,17-diacetoxy-3-ethoxyestra-1,3,5(10),16-tetraene and 1,17-diacetoxy-3-butoxyestra-1,3,5(10),16-tetraene are employed in place of 1,17-diacetoxy-3-methoxyestra-1,3,5(10),16-tetraene, 1-acetoxy-16α-chloro-3-ethoxyestra-1,3,5(10)-trien-17one and 1-acetoxy-3-butoxy-16α-chloroestra-1,3,5(10)-trien-17-one are obtained.

EXAMPLE 12

1,17β-Diacetoxy-16α,17α-epoxy-3-methoxyestra-1,3,5(10)-triene

A solution of m-chloroperbenzoic acid (1.38 g, 8.5 mM) in 60 ml of methylene chloride is added over a period of 30 min to a solution of 1,17-diacetoxy-3-methoxyestra-1,3,5(10),16-tetraene (1.54 g, 4 mM) in 60 ml of methylene chloride. Stirring is continued at room temperature for an additional 30 mins and the excess peracid is neutralized by the addition of 100 ml of 10% sodium thiosulfate. The layers are separated and the organic layer is washed with 2 × 50 ml saturated $NaHCO_3$ and 2 × 25 ml $H_2O$ and then dried over $Na_2SO_4$.

Evaporation of the solvent in vacuo gives an oily residue which is chromatographed on 75 g of neutral silica gel. The column is eluted initially with chloroform gradually increasing the polarity to 15% ethyl acetate:chloroform. The initial fractions give 1,17β-diacetoxy-16α,17α-epoxy-3-methoxyestra-1,3,5(10)-triene, yield 0.205 g (13%); m.p. 152°–154° (methanol-$H_2O$).

When in the above procedure 3-butoxy-1,17-dipropionyloxyestra-1,3,5(10),16-tetraene and 1,17-dipropionyloxy-3-ethoxyestra-1,3,5(10),16-tetraene are employed in place of 1,17-diacetoxy-3-methoxyestra-1,3,5(10),16-tetraene, 3-butoxy-1,17β-dipropionyloxy-16α,17α-epoxyestra-1,3,5(10)-triene and 1,17β-dipropionyloxy-16α,17α-epoxy-3-ethoxyestra-1,3,5(10)-triene are obtained.

EXAMPLE 13

1-Acetoxy-16α-hydroxy-3-methoxyestra-1,3,5(10)-trien-17-one

Further elution of the column prepared in Example 12 gives 1-acetoxy-16α-hydroxy-3-methoxyestra-1,3,5(10)-trien-17-one, yield 0.65 g (45%); m.p. 228°–231° (methanol).

EXAMPLE 14

1-Acetoxy-16α-bromo-3-methoxyestra-1,3,5(10)-trien-17-one

A solution of $Br_2$ (0.4 g, 2.5 mM) in 10 ml of carbon tetrachloride is added over a period of 5 min to a suspension of 1,17-diacetoxy-3-methoxyestra-1,3,5(10),16-tetraene (0.95 g, 2.5 mM), potassium carbonate (0.53 g) and 40 ml of carbon tetrachloride at 0°. After an additional 5 min the colorless suspension is added to a solution of $NaHSO_3$ (1 g) in 75 ml of $H_2O$. The layers are separated and the aqueous layer is extracted with 3 × 25 ml of chloroform, the organic layers are combined and evaporated in vacuo after drying with $MgSO_4$. Trituration of the residue with a small amount of methanol gives 1-acetoxy-16α-bromo-3-methoxyestra-1,3,5(10)-trien-17-one, yield 0.94 g (90%); m.p. 188°–190° (methanol).

When in the above procedure 17-acetoxy-3-ethoxy-1-valeryloxyestra-1,3,5(10),16-tetraene and 17-acetoxy-3-butoxy-1-propionyloxyestra-1,3,5(10),16-tetraene are employed in place of 1,17-diacetoxy-3-methoxyestra-1,3,5(10),16-tetraene, 16α-bromo-3-ethoxy-1-valeryloxyestra-1,3,5(10)-trien-17-one and 16α-bromo-3-butoxy-1-propionyloxyestra-1,3,5(10)-trien-17-one are obtained.

EXAMPLE 15

1-Acetoxy-16β-chloro-3-methoxyestra-1,3,5(10)-trien-17-one

A solution of lithium chloride (1.3 g, 31 mM) in 9 ml of anhydrous dimethylformamide is heated to 70° and then cooled to room temperature. 1-Acetoxy-16α-bromo-3-methoxyestra-1,3,5(10)-trien-17-one (0.50 g) is added to the solution as a solid using Gooch tubing. The resulting suspension is heated to 50° to effect solution. The solution is then stirred at room temperature for 5 hr, poured into 100 ml of $H_2O$, filtered and dried in vacuo to give a white solid. Recrystallization from methanol gives 1-acetoxy-16β-chloro-3-methoxyestra-1,3,5(10)-trien-17-one, yield 0.40 g (89%); m.p. 164°–166°.

When in the above procedure 1-acetoxy-16α-bromo-3-ethoxyestra-1,3,5(10)-trien-17-one and 16α-bromo-3-butoxy-1-propionyloxyestra-1,3,5(10)-trien-17-one are employed in place of 1-acetoxy-16α-bromo-3-methoxyestra-1,3,5(10)-trien-17-one, 1-acetoxy-16β-chloro-3-ethoxyestra-1,3,5(10)-trien-17-one and 3-butoxy-16β-chloro-1-propionyloxyestra-1,3,5(10)-trien-17-one are obtained.

EXAMPLE 16

3-Methoxy-1-propionyloxyestra-1,3,5(10)-trien-17-one

A solution of 1-hydroxy-3-methoxyestra-1,3,5(10)-trien-17-one (2.3g, 10 mM) in 50 ml of anhydrous pyridine is treated with 5 ml of propionic anhydride at room temperature for 24 hrs. The crude reaction mixture is evaporated in vacuo and the residue is partitioned between ether and brine. The ethereal layer is washed with a solution of copper sulfate, cold $H_2O$ and dried over sodium sulfate. Evaporation of the solvent affords 3-methoxy-1-propionyloxyestra-1,3,5(10)-trien-17-one.

When in the above procedure butyric anhydride, valeric anhydride and caproic anhydride are employed in place of propionic anhydride, 1-butyryloxy-3-methoxyestra-1,3,5(10)-trien-17-one, 3-methoxy-1- valeryloxyestra-1,3,5(10)-trien-17-one and 1-caproyloxy-3-methoxyestra-1,3,5(10)-trien-17-one, respectively, are obtained.

EXAMPLE 17

1-Acetoxy-3-methoxy-17-propionyloxyestra-1,3,5(10),16-tetraene

A solution of 1-acetoxy-3-methoxyestra-1,3,5(10)-trien-17-one (0.884 g, 26 mM), isopropenyl propionate (15.1 g, 123 mM) and p-toluenesulfonic acid monohydrate (0.134 g, 0.7 mM) is heated at 120° on a set-up employing a Vigreaux column as described in Example 9. After heating at 120° for 12 hrs, the temperature is raised to 150° for 1 hr. The pot residue is poured into ether. The ethereal solution is extracted with saturated sodium bicarbonate solution, cold $H_2O$ and dried over $MgSO_4$. Evaporation of the solvent gives a residue which upon chromatography on neutral silica gel affords 1-acetoxy-3-methoxy-17-propionyloxyestra-1,3,5(10),16-tetraene.

The starting materials used to prepare the novel compounds of this invention are prepared as follows:

PREPARATION I

1-Acetoxy-3-methoxyestra-1,3,5(10)-trien-17-one

1-Acetoxy-3-hydroxyestra-1,3,5(10)-trien-17-one (7.6 g, 23 mM) is added to 600 ml of anhydrous acetone in a 3-neck, 1 liter round bottom flask equipped with condenser, magnetic stirring bar, drying tube and pressure-compensated addition funnel. Dimethyl sulfate (3.2 g, 25 mM) is added and the resulting suspension is refluxed for 16 hrs, and then filtered while still warm. The filter cake is washed repeatedly with anhydrous acetone, and the combined filtrates are evaporated in vacuo. The residue is recrystallized from acetone-water to obtain 1-acetoxy-3-methoxyestra-1,3,5(10)-trien-17-one, yield 6.2 g (80%), m.p. 144°–145°. Further recrystallization from $CH_2Cl_2$-hexane gives material of m.p. 150°–151°.

PREPARATION II

1-Hydroxy-3-methoxyestra-1,3,5(10)-trien-17-one

A solution of 1-acetoxy-3-methoxyestra-1,3,5(10)-trien-17-one (7.0 g, 20.5 mM) in 150 ml of 5% anhydrous methanolic potassium hydroxide is stirred at room temperature for 1 hr. The resulting dark purple solution is added to 700 ml of cold $H_2O$ and acidified with 10% HCl to give a white solid which is filtered and recrystallized from acetone-$H_2O$ to give 1-hydroxy-3-methoxyestra-1,3,5(10)-trien-17-one, yield 5.4 g (88%), m.p. 220°–222°. Further recrystallization from ethyl acetate gives a product with a m.p. 226°–229°.

PREPARATION III

1,3-Dimethoxyestra-1,3,5(10)-trien-17-one

A suspension of 1-hydroxy-3-methoxyestra-1,3,5(10)-trien-17-one (2.5 g, 8.3 mM), dimethyl sulfate (1.3 g, 10.3 mM) and potassium carbonate (1.2 g) in 250 ml of anhydrous acetone is refluxed with vigorous stirring for 6 hrs. An additional 0.5 g of dimethyl sulfate is added and the suspension refluxed for 14 hrs. The reaction mixture is filtered while warm and the solids washed well with acetone. The combined acetone filtrates are evaporated in vacuo and the residue is recrystallized from methanol-$H_2O$. Two recrystallizations give 1,3-dimethoxyestra-1,3,5(10)-trien-17-one, yield 1.91 g (73%); m.p. 132°–133°.

PREPARATION IV

1,3-Dihydroxyestra-1,3,5(10)-trien-17-one

A solution of 1-acetoxy-3-hydroxy-1,3,5(10)-trien-17-one (9.7 g, 30 mM) in 200 ml of 5% methanolic potassium hydroxide is stirred at room temperature for 30 min. The solution is then poured into 1500 ml of cold $H_2O$ and acidified with 10% HCl. The white solid which forms is collected by filtration and recrystallization from methanol-$H_2O$ gives 1,3-dihydroxyestra-1,3,5(10)-trien-17-one, yield 7.6 g (90%); m.p. 245°–247°.

What is claimed is:

1. A compound of the formula:

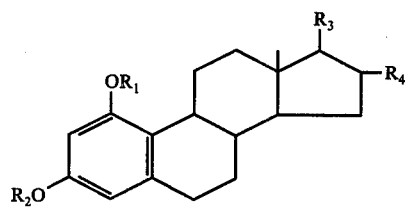

wherein $R_1$ is lower alkanoyl wherein the alkyl group has 2–6 carbon atoms; lower alkyl wherein the alkyl group has 1–5 carbon atoms and trialkylaminosulfoxy wherein the alkyl group has 1–3 carbon atoms; $R_2$ is lower alkyl wherein the alkyl group has 1–5 carbon atoms and trialkylaminosulfoxy wherein the alkyl group has 1–3 carbon atoms; $R_3$ is oxo, cyanoethoxy and trifluoroalkanoyloxy wherein the alkanoyloxy group has 2–5 carbon atoms; and $R_4$ is halo, hydrogen, lower alkanoyloxy wherein the alkanoyloxy group has 2–5 carbon atoms and hydroxy; provided that when $R_3$ is oxo, one of $R_1$ or $R_2$ is trialkylaminosulfoxy.

2. The compound of claim 1 which compound is 3-methoxy-1-sulfooxyestra-1,3,5(10)-trien-17-one triethylammonium salt.

3. The compound of claim 1 which compound is 1-acetoxy-3-sulfooxyestra-1,3,5(10)-trien-17-one triethylammonium sulfate.

4. The compound of claim 1 which compound is 1-acetoxy-16α-chloro-3-methoxyestra-1,3,5(10)-trien-17-one.

5. The compound of claim 1 which compound is 17β-(2-cyanoethoxy)-1,3-dimethoxyestra-1,3,5(10)-triene.

6. The compound of claim 1 which compound is 1-acetoxy-3-methoxy-17β-trifluoroacetoxyestra-1,3,5(10)-triene.

7. The compound of claim 1 which compound is 1-acetoxy-16α-bromo-3-methoxyestra-1,3,5(10)-trien-17-one.

8. A method of suppressing reproduction which comprises administering to female animals an effective amount of a compound of the formula:

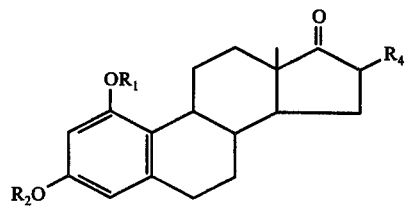

-continued

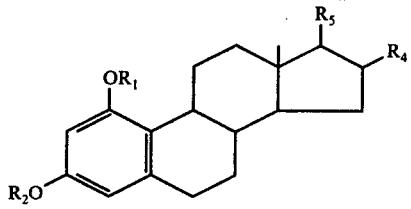

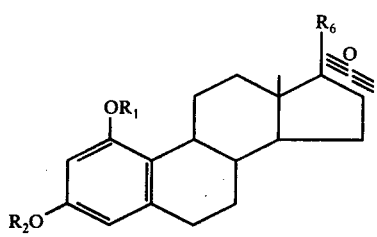

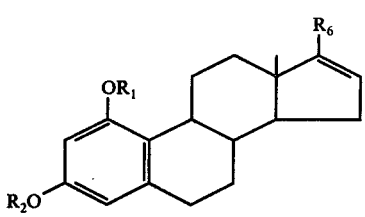

wherein
R₁ is lower alkanoyloxy, lower alkyl and trialkylaminosulfoxy;
R₂ is lower alkyl and trialkylaminosulfoxy;
R₄ is hydrogen, halogen, lower alkanoyloxy and hydroxy;
R₅ is lower alkoxy, lower alkanoyloxy, hydroxy, cyanoethoxy and trifluoroalkanoyloxy; and
R₆ is hydroxy and lower alkanoyloxy.

9. A method of suppressing reproduction which comprises administering to female animals an effective amount of a compound of the formula:

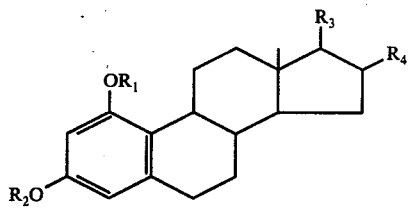

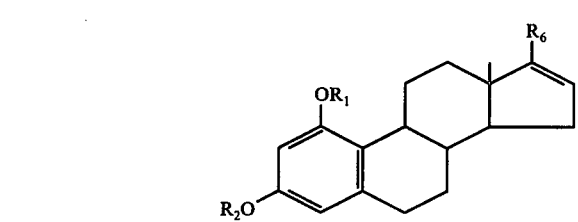

wherein
R₁ is lower alkanoyl, lower alkyl and trialkylaminosulfoxy;
R₂ is lower alkyl and trialkylaminosulfoxy;
R₃ is oxo, lower alkanoyloxy, lower alkoxy, hydroxy, cyanoethoxy and trifluoroalkanoyloxy; and R₄ is halogen, lower alkanoyloxy and hydroxy, provided that when R₃ is other than oxo, R₄ may also be hydrogen, except that where R₁ and R₂ are trialkylaminosulfoxy, R₃ may be oxo and R₄ may be hydrogen; and
R₆ is hydroxy or lower alkanoyloxy.

10. The process for the preparation of a compound of the formula:

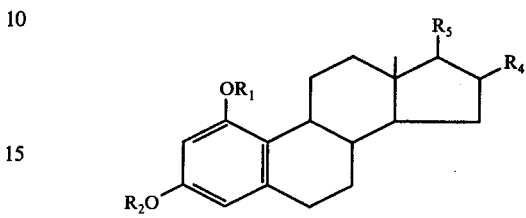

which comprises reacting a compound of the formula:

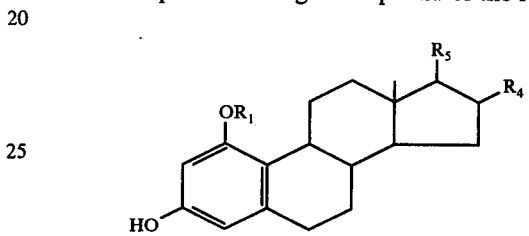

with a sulfur trioxide triethylamine complex, wherein
R₁ is lower alkanoyl and lower alkyl;
R₂ is trialkylaminosulfoxy;
R₄ is hydrogen, halogen and lower alkanoyloxy;
R₅ is lower alkanoyloxy, lower alkoxy, cyanoethoxy and trifluoroalkanoyloxy.

11. The process for the preparation of a compound of claim 1 of the formula:

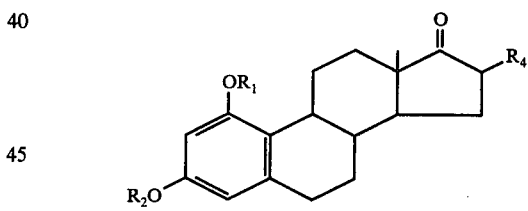

which comprises reacting a compound of the formula:

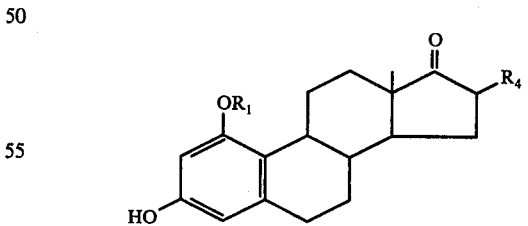

with a sulfur trioxide triethylamine complex; wherein
R₁ is lower alkanoyl and lower alkyl;
R₂ is trialkylaminosulfoxy;
R₄ is hydrogen, halogen and lower alkanoyloxy.

* * * * *

UNITED STATES PATENT AND TRADEMARK OFFICE
CERTIFICATE OF CORRECTION

PATENT NO. : 4,096,253
DATED : June 20, 1978
INVENTOR(S) : Michael P. Wachter and Joseph A. Settepani It is certified that error appears in the above-identified patent and that said Letters Patent are hereby corrected as shown below:

In Column 3, line 56, "with $CH_2H_2$," should read ---$CH_2N_2$,---
In Column 5, line 12, "1,3,5-(10)-triene" should read
---1,3,5(10)-triene---
In Column 7, line 10, "$CCl_4$at 0°." should read ---$CCl_4$ at 0°.---
In Column 7, line 25, "trien-17one" should read ---trien-17-one---

Signed and Sealed this

Thirteenth Day of February 1979

[SEAL]

Attest:

RUTH C. MASON
Attesting Officer

DONALD W. BANNER
Commissioner of Patents and Trademarks